United States Patent
Charrier et al.

(10) Patent No.: US 6,929,918 B1
(45) Date of Patent: Aug. 16, 2005

(54) METHOD FOR DIAGNOSING AN ADENOCARCINOMA OR A BENIGN PROSTATE PATHOLOGY

(75) Inventors: Jean-Philippe Charrier, Ecully (FR); Carole Tournel, Chasselay (FR); Michel Jolivet, Saint Bonnet de Mure (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/720,717
(22) PCT Filed: Jul. 5, 1999
(86) PCT No.: PCT/FR99/01622
§ 371 (c)(1),
(2), (4) Date: Jan. 23, 2001
(87) PCT Pub. No.: WO00/02052
PCT Pub. Date: Jan. 13, 2000

(30) Foreign Application Priority Data

Jul. 3, 1998 (FR) .............................. 98 08702

(51) Int. Cl.[7] .............................. G01N 33/53
(52) U.S. Cl. .................. 435/7.1; 435/7.23; 435/7.4; 435/7.41; 530/350; 424/184.1; 424/185.1
(58) Field of Search ................. 435/7.1, 7.23, 435/962, 7.4, 7.91; 436/501; 530/350; 424/184.1, 185.1

(56) References Cited

FOREIGN PATENT DOCUMENTS

WO    WO 97/12245    4/1997

OTHER PUBLICATIONS

Kumar. Cancer Res. 56: 5397–5402, 1996.*
Wald, HJ Br. J. Cancer, 82:731–6, 2000.*
Carter, Urol. 55: 796–9, 2000.*
Jung, K. Intl J Cancer, 93(5): 759–65, 2001.*
Lien et al, 1998, Cancer Investigation, 16(1):45–49.*
Mikolajcyk, S et al, 1997, Urology, 50(5): 710–714.*
Chen, Z et al, 1997, J Urology, 157: 2166–2170.*
Taber's cyclopedia medical dictionary, 1989, 16th ed, p.867, 870.*
Tockman et al (Cancer Res., 1992, 52:2711s–2718s).*
Z. Chen et al., "Prostate Specific Antigen Benign Prostatic Hyperplasia: Purification And Characterization", Journal of Urology, vol. 157, No. 6, 1997, pp. 2166–2170, Stanford CA USA.
Van Cangh et al., "Free to Total Prostate–Specific Antigen (PSA) Ration is Superior to Total–PSA in Differentiating Benign Prostate Hypertrophy From Prostate Cancer", The Prostate Supplement 7:30–34 (1996).

* cited by examiner

*Primary Examiner*—Susan Ungar
*Assistant Examiner*—Minh-Tam Davis
(74) *Attorney, Agent, or Firm*—Oliff & Berridge, PLC (57) ABSTRACT

The invention concerns a method for diagnosing a prostate adenocarcinoma in a male human patient without performing a prostatic biopsy, using the PSA protein (prostate specific antigen) present in the patient's blood, serum, urine or seminal fluid that involves measuring the free PSA total level, i.e., cleaved and non-cleaved; measuring the level of all or part of the cleaved free PSA; calculating the proportion of cleaved free PSA relative to the total free PSA, non-cleaved free PSA to free PSA, and/or cleaved free PSA to any of non-cleaved free, total, or complexed PSA; and diagnosing that the patient suffers from a prostate adenocarcinoma when the ratio used is not more than a reference value or a benign pathology when the ratio used is higher than the reference value.

10 Claims, 4 Drawing Sheets

METHOD FOR DIAGNOSING AN ADENOCARCINOMA OR A BENIGN PROSTATE PATHOLOGY

The present application is the National Phase Application of International Application No. PCT/FR99/01622, filed Jul. 5, 1999.

BACKGROUND OF THE INVENTION

1. Field of Invention

The present invention relates to a method of screening or diagnosis which makes it possible to detect the presence of a prostate cancer or of a benign prostate hyperplasia (BPH) in a patient, this being without performing a biopsy.

2. Description of Related Art

Indeed, the prostate specific antigen, more commonly called PSA, is the principal marker for prostate cancer which will affect, during one's life, one man out of six in the West. This protease of the kallikrein family, mainly secreted by the prostatic epithelium, is found at a concentration of 0.5 to 5 mg/ml in the seminal fluid and at a concentration one million times lower in the serum of a patient. This serum PSA level increases markedly during a prostate cancer and moderately during benign impairments, such as BPH, acute prostatitis, and the like.

However, the area of overlap between the various pathologies is responsible for a substantial lack of sensitivity and of specificity. Accordingly, 30 to 45% of cancers confined to the gland, which constitutes an early and potentially curable stage, are not detected with the usual threshold of 4 ng/ml whereas three patients out of four are wrongly suspected.

In addition, it has recently been shown that in serum, PSA combined with protease inhibitors such as $\alpha$-1-antichymostrypsin (ACT), and that the use of the free PSA to total PSA ratio made it possible to improve the specificity of the diagnosis.

The prior art therefore shows that techniques exist which make it possible to diagnose the development of a prostate cancer in patients. Thus, patent application WO-A-97/12245 claims a method which makes it possible to diagnose an adenocarcinoma of the prostate (CAP) without biopsy. This method consists in measuring, in the serum or in the blood of patients, the total quantity of PSA. If this value is between 2.5 and 20 ng/ml, the concentration of free PSA is also measured. The free PSA to total PSA ratio is then calculated. If this ratio is less than 7%, the diagnosis is oriented toward an adenocarcinoma of the prostate.

However, the use of a 7% threshold for the diagnosis of a cancer of the prostate is much debated by many authors, as shown by the publication by Lein et al. "Relation of free PSA/total PSA in serum for differentiating between patients with prostatic cancer and benign prostate hyperplasia: which cutoff should be used?". In this document published in the journal Cancer Investigation, 16(1), 45–49, 1998, it has been shown that it is difficult to systematically differentiate a cancer or adenocarcinoma of the prostate from a BPH by means of this ratio.

In addition, the publication by Catalona et al., "Prostate Cancer Detection in Men With Serum PSA Concentrations of 2.6 to 4.0 ng/ml and Benign Prostate Examination", published in JAMA of 14 May 1997-Vol. 277, No. 18, demonstrates a concentration less than 4 ng/ml should be taken into consideration in order to make an early diagnosis of a cancer of the prostate.

Moreover, in the seminal fluid, PSA may have internal cleavage sites which do not affect its three-dimensional cohesion because of the existence of five disulfide bridges which link the various fragments of the molecule. The PSA thus cleaved loses its enzymatic activity and its capacity to bind to protease inhibitors. However, in the serum, no cleaved form is generally mentioned in the prior state of the art.

No cleaved form has so far been reported in cases of benign pathologies of the prostate and the value of the cleaved forms has not been explored for diagnostic purposes.

SUMMARY OF THE INVENTION

In accordance with the present invention, the diagnostic method proposed makes it possible to compensate for the lack of efficacy of the tests in the total PSA concentration region greater than 2 ng/ml. To this end, the molecular forms of serum PSA of patients suffering from cancer or from BPH have been mapped by two-dimensional electrophoresis, combined with chemi-luminescence detection, in order to observe all the forms of PSA, free, complexed and cleaved.

Thus, the serum profiles of cancer sufferers are relatively homogeneous, whereas those for BPH may comprise a relatively large proportion of cleaved forms, and of slightly more basic spots.

It is therefore established that the increase in the free PSA to total PSA ratio in the case of BPH may be linked to the existence of cleaved PSA which is enzymatically inactive and incapable of binding to ACT, or may be in relationship with slightly basic free PSA which may correspond to the inactive zymogenic form.

To this effect, the present invention relates to a first method of analysis for the purpose of the diagnosis of an adenocarcinoma of the prostate in a male human patient, without performing prostate biopsy, which uses the PSA (prostate specific antigen) protein present in a blood, serum, urine or seminal fluid sample from the patient, characterized in that it consists in:

measuring the level of total free PSA, that is to say cleaved or noncleaved, measuring the level of all or part of the cleaved free PSA, calculating the proportion of cleaved free PSA relative to the total free PSA, and distinguishing two cases, namely:
  this ratio has a value less than or equal to a reference or differentiating value, found in patients suffering from an adenocarcinoma of the prostate, such that the patient is suffering from an adenocarcinoma of the prostate,
  this ratio has a value greater than the reference value, found in patients suffering from a benign pathology of the prostate, such that the patient is suffering from a benign pathology of the prostate, such as a benign prostate hyperplasia.

The present invention relates to a second method of analysis for the purpose of the diagnosis of an adenocarcinoma of the prostate in a male human patient, without performing prostate biopsy, which uses the PSA (prostate specific antigen) protein present in a blood, serum, urine or seminal fluid sample from the patient, characterized in that it consists in:

measuring the level of noncleaved free PSA,
measuring the level of all or part of the cleaved free PSA, calculating the proportion of cleaved free PSA relative to the noncleaved free PSA, and distinguishing two cases, namely:
    this ratio has a value less than or equal to a reference or differentiating value, found in patients suffering from an adenocarcinoma of the prostate, such that the patient is suffering from an adenocarcinoma of the prostate,
    this ratio has a value greater than the reference value, found in patients suffering from a benign pathology of the prostate, such that the patient is suffering from a benign pathology of the prostate, such as a benign prostate hyperplasia.
In these first two cases, the reference value is between 2 and 12% and preferably between 5 and 8%.

The present invention relates to a third method of analysis for the purpose of the diagnosis of an adenocarcinoma of the prostate in a male human patient, without performing prostate biopsy, which uses the PSA (prostate specific antigen) protein present in a blood, serum, urine or seminal fluid sample from the patient, characterized in that it consists in:
measuring the level of total free PSA, that is to say cleaved or noncleaved,
measuring the level of all or part of the noncleaved free PSA,
calculating the proportion of noncleaved free PSA relative to the total free PSA, and
distinguishing two cases, namely:
    this ratio has a value greater than or equal to a reference or differentiating value, found in patients suffering from an adenocarcinoma of the prostate, such that the patient is suffering from an adenocarcinoma of the prostate,
    this ratio has a value lower than the reference value, found in patients suffering from a benign pathology of the prostate, such that the patient is suffering from a benign pathology of the prostate, such as a benign prostate hyperplasia.
In this third case, the reference value is between 88 and 98% and preferably between 93 and 95%.

The present invention relates to a fourth method of analysis for the purpose of the diagnosis of an adenocarcinoma of the prostate in a male human patient, without performing prostate biopsy, which uses the PSA (prostate specific antigen) protein present in a blood, serum, urine or seminal fluid sample from the patient, characterized in that it consists in:
measuring the level of total PSA, that is to say complexed and free (cleaved or noncleaved),
measuring the level of all or part of the cleaved free PSA,
calculating the proportion of cleaved free PSA relative to the total PSA, and
distinguishing two cases, namely:
    this ratio has a value less than or equal to a reference or differentiating value, found in patients suffering from an adenocarcinoma of the prostate, such that the patient is suffering from an adenocarcinoma of the prostate,
    this ratio has a value greater than the reference value, found in patients suffering from a benign pathology of the prostate, such that the patient is suffering from a benign pathology of the prostate, such as a benign prostate hyperplasia.
In this fourth case, the reference value is between 0.1 and 2% and preferably between 0.4 and 1%.

The present invention relates to a first method of analysis for the purpose of the diagnosis of an adenocarcinoma of the prostate in a male human patient, without performing prostate biopsy, which uses the PSA (prostate specific antigen) protein present in a blood, serum, urine or seminal fluid sample from the patient, characterized in that it consists in:
measuring the level of PSA complexed,
measuring the level of all or part of the cleaved free PSA,
calculating the proportion of cleaved free PSA relative to the complexed PSA, and
distinguishing two cases, namely:
    this ratio has a value greater than or equal to a reference or differentiating value, found in patients suffering from an adenocarcinoma of the prostate, such that the patient is suffering from an adenocarcinoma of the prostate,
    this ratio has a value less than the reference value, found in patients suffering from a benign pathology of the prostate, such that the patient is suffering from a benign pathology of the prostate, such as a benign prostate hyperplasia.
In this fifth case, the reference value is between 0.1 and 2.2%, preferably between 0.6 and 1.2%.

The present invention relates to a sixth method of analysis for the purpose of the diagnosis of an adenocarcinoma of the prostate in a male human patient, without performing prostate biopsy, which uses the PSA (prostate specific antigen) protein present in a blood, serum, urine or seminal fluid sample from the patient, characterized in that it consists in:
measuring the level of noncleaved free PSA,
measuring the level of all or part of the cleaved free PSA,
measuring the level of free PSA,
measuring the level of total PSA,
calculating the proportion of cleaved free PSA relative to the noncleaved free PSA, called first ratio,
calculating the proportion of free PSA relative to the total PSA, called second ratio, and
distinguishing four cases, namely:
    this first ratio has a value less than or equal to a first reference or differentiating value and this second ratio has a value less than or equal to a second reference or differentiating value, such that the patient is suffering from an adenocarcinoma of the prostate,
    this first ratio has a value greater than or equal to a first reference or differentiating value and this second ratio has a value greater than or equal to a second reference or differentiating value, such that the patient is suffering from a benign pathology of the prostate, such as a benign prostate hyperplasia,
    this first ratio has a value less than or equal to a first reference or differentiating value and this second ratio has a value greater than or equal to a second reference or differentiating value, such that the patient has a high probability of suffering from an adenocarcinoma of the prostate and a low probability of suffering from a benign pathology of the prostate, such as a benign prostate hyperplasia,
    this first ratio has a value greater than or equal to a first reference or differentiating value and this second ratio has a value less than or equal to a second reference or differentiating value, such that the patient has a high probability of suffering from a benign pathology of the prostate, such as a benign prostate hyperplasia, and a low probability of suffering from an adenocarcinoma of the prostate.
In this sixth case, the first reference value is between 1 and 18%, preferably between 5 and 8% and more precisely is substantially 6.3% and the second reference value is between 10 and 20%, preferably between 13 and 17% and more precisely is substantially 15%.

Preferably, in the context of this sixth case, the high probability of suffering from an adenocarcinoma of the prostate is between 80 and 95% and preferably between 84 and 87% and the low probability of suffering from a benign pathology of the prostate is between 5 and 20% and preferably between 13 and 16%, whereas the high probability of suffering from a benign pathology of the prostate is between 80 and 95% and preferably between 82 and 85%, and the low probability of suffering from an adenocarcinoma of the prostate is between 5 and 20% and preferably between 15 and 18%.

The present invention also relates to a method of analysis for the diagnosis of an adenocarcinoma or of a benign pathology of the prostate in a patient, which uses a combination of at least two methods described above.

According to a variant embodiment, it is carried out when the total PSA concentration in the blood or in the serum is greater than 2 ng/ml.

The present invention finally relates to a process using one of the methods which have just been described; it consists in:
detecting the presence and quantifying the free PSA in cleaved form or in noncleaved form, and
determining the value of the proportion of cleaved free PSA relative to the total free PSA, relative to a reference value.

The proteins derived from the blood, serum, urine or seminal fluid from the patient are subjected to migration beforehand.

Preferably, the migration is carried out by two-dimensional electrophoresis.

The level of total PSA is assayed beforehand.

Finally and preferably, the detection is carried out by chemiluminescence after visualization by Western blotting.

BRIEF DESCRIPTION OF THE DRAWINGS

The accompanying figures are given by way of explanatory example and have no limiting character. They will make it possible to understand the invention more clearly.

Finally.

DETAILED DESCRIPTION OF PREFERRED EMBODIMENTS

The present invention relates to a method for the diagnosis of prostate cancer or of benign pathology of the prostate, such as BPH, by means of the treatment of 100 µl in the following manner:
addition of 50 µl of solution in water of sodium dodecyl sulfate (SDS) at 10% and of dithiothreitol (DTT) at 2.3%;
heating for 5 minutes on a boiling water bath;
dilution in QS 350 µl of solution in water of 8.3 M urea, 2 M Thiourea, 4% 3-[(3-cholamidopropyl)dimethylammonio]-1-propanesulfonate (CHAPS), 100 mM DTT, 2% Servalyte 4–9 (Serva, Heidelberg, Germany), 0.1 g/l Orange G;
rehydration in a test tube under paraffin oil for 6 to 72 hours at room temperature of a dry Immobiline strip having a nonlinear immobilized pH gradient between pH=3 and pH=10 (Pharmacia, Uppsalla, Sweden) with the aid of 500 µl of dilute sample;
migration and focusing of the proteins in the sample as a function of their isoelectric point in the Immobiline strip with the aid of the Multiphore II system (Pharmacia) in accordance with the supplier's recommendations at 15° C. and over 100 kV/h at more or less 10% at 6 000 V in order to carry out a separation in the first dimension;
freezing of the focused Immobiline strip at −30° C. (optional);
equilibration of the Immobiline strip for a period of 15 minutes in a solution containing 1.5 M Tris(hydroxymethyl)aminomethane, hydrochloric acid pH=8.8 supplemented with 6 M urea, 2% SDS, 30% Glycerol, 50 mg/ml Bromophenol Blue and 10 mg/ml DTT;
equilibration of the Immobiline strip for a period of 15 minutes in a solution containing 1.5 M Tris(hydroxymethyl)aminomethane, hydrochloric acid pH=8.8 supplemented with 6 M urea, 2% SDS, 30% glycerol, 50 mg/ml Bromophenol Blue and 480 mg/ml Iodoacetamide;
draining for 5 to 10 minutes on a moist blotting paper of the excess equilibrating solution by depositing the Immobiline strip on the section;
deposition of the Immobiline strip at the top of a polyacrylamide gel, C=2.8%, T=12% of 16×20 cm;
covering the Immobiline strip with a 0.5% molten agarose solution in buffer containing 25 mM Tris(hydroxymethyl) aminomethane, 192 mM glycine, 1% SDS, at pH=8.4;
migration as a function of their molecular weight of the proteins previously focused in the Immobiline strip in the polyacrylamide gel with the aid of the Protean II xi system (Bio-Rad, Hercules, United States of America) in accordance with the supplier's recommendations in order to carry out a separation in the second dimension;
transfer of the proteins from the two-dimensional gel to an Immobilon-P membrane (Millipore, Bedford, United States of America) with the aid of the Trans-blot system (Biorad) in a solution of 10 mM 3-[cyclohexyl-amino]-1-propanesulfonic acid (CAPS). 10% methanol at pH=11 for 16 to 24 hours at 400 mA;
passivation for 1 hour of the binding sites which have remained free on the membrane with the aid of the TNTM solution (15 mM Tris(hydroxymethyl)aminomethane, 0.14 M NaCl, 0.5 ml/l Tween 20, pH=8.0 supplemented with 5% freeze-dried skimmed milk);

incubation for 1 hour of the membrane in a dilution containing 10 µg/ml of mouse monoclonal antibody clone 13C9E9D6G8 (Bio-Mérieux) in TNTM solution;

washing the membrane 3 times 10 minutes in TNTM solution;

incubation, for 1 hour, of the membrane in a 1/5 000 dilution of goat polyclonal antibody anti-mouse Fc coupled to horseradish peroxidase (Jackson ImmunoResearch, West Gove, United States of America) in TNTM solution;

washing the membrane for twice 10 minutes in TNTM solution;

washing the membrane for 10 minutes in a solution containing 0.1 M Tris(hydroxymethyl)aminomethane, hydrochloric acid pH=7.6;

visualizing with the aid of the chemiluminescent substrate of horseradish peroxidase Super Signal Ultra (Pierce, Rockford, United States of America) according to the supplier's recommendations;

detection of the light emitted with the aid of the FluorS Multi-Imager system (Bio-Rad) for 1 minute to 1 hour with a scale of 4096 levels of gray;

quantification of the cleaved and noncleaved free PSA forms with the aid of the MultiAnalyst software (Bio-Rad);

calculation of the proportions of cleaved free PSA relative to the total free PSA, or of the noncleaved free PSA relative to the total free PSA, or of the cleaved free PSA relative to the noncleaved free PSA, or of the cleaved PSA relative to the total PSA, or of the PSA relative to the complexed PSA;

determination of the diagnosis of prostate cancer according to the reference values previously described.

The invention therefore relates to a method for the diagnosis of an adenocarcinoma of the prostate but also to a method which makes it possible to differentiate a patient suffering from an adenocarcinoma of the prostate from a patient suffering from a benign pathology of the prostate, such as for example a benign prostate hyperplasia (BPH).

Figure 1:
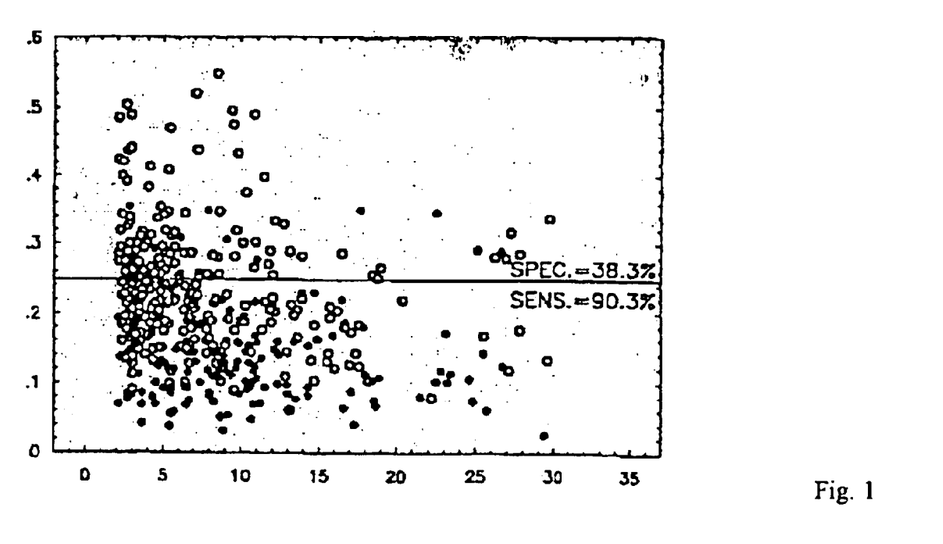
FIG. 1 represents a comparative table of the position of sera from different patients as a function, on the one hand, of their total PSA concentration, which is between 2.1 and 30 ng/ml (x-axis), and, on the other hand, of their free PSA to total PSA ratio (y-axis). This table is taken from an article "Free to total Prostate-Specific Antigen (PSA) ratio is superior to total-PSA in differentiating Benign prostate hyperplasia from prostate cancer", Vol. 156, 1964–1968, Dec. 1996, according to P. J. Van Cangh et al. The filled circles represent the cancer cases and the open circles the BPH cases.

Thus, as is clearly represented in FIG. 1, filled circles and open circles are represented. The filled circles represent cases of cancers whereas the open circles relate to BPHs. It can be noted essentially that there is a complete blend between the cancer cases and the BPH cases. It is therefore difficult with a free PSA to total PSA ratio to really calculate if cancer or BPH exists. An important point will however be noted, namely that the great majority of cancer and BPH cases, which are presented later, is above a concentration of 2.1 ng/ml of total PSA. That is the case for seventy-four of the seventy-five sera from patients tested. Only patient 35 has a value less than 1.27 ng/ml. As a general rule, it will therefore be logical to think that below this threshold, the cancer or BPH cases are not very frequent. The patients having a total PSA concentration of less than 2 ng/ml are considered to be healthy. The risk of their having a BPH is not quantifiable because the number of cases analyzed is too small to be significant.

The present invention therefore consists in differentiating cancer and BPH. To happen, two-dimensional electrophoreses are carried out as represented for example in FIG. 2. Three proteins or polypeptides of different sizes are observed on this electrophoresis. There is first of all, in the top portion, a protein of substantially 34 kD, at more or less 20%, which in fact corresponds to the noncleaved PSA protein.

Figure 2:
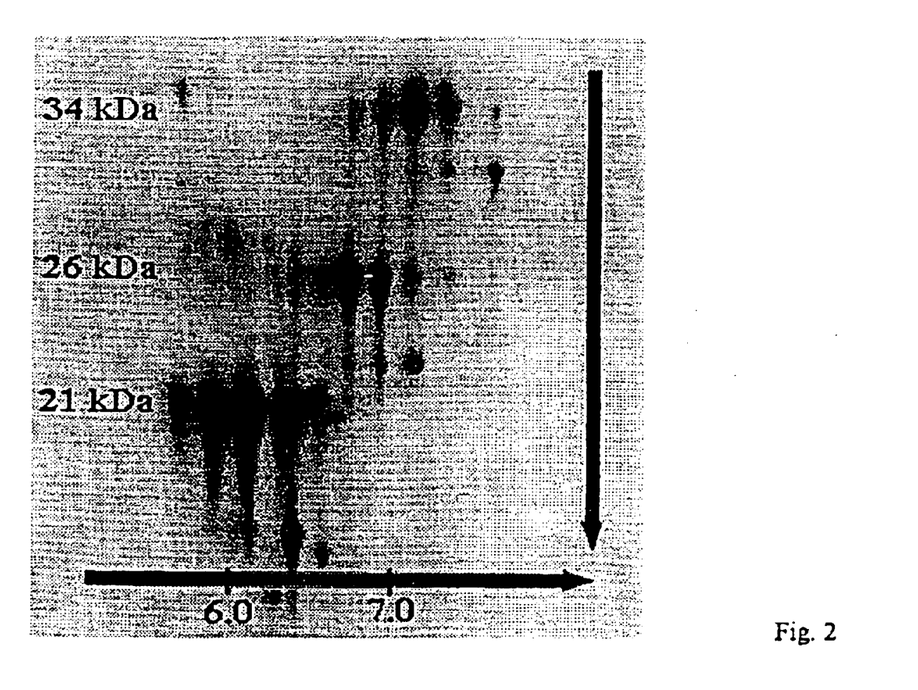
FIG. 2 represents a two-dimensional electrophoresis, stained with silver nitrate, where the migration of PSA, in various forms, is carried out as a function, on the one hand, of the isoelectric point on the x-axis, and, on the other hand, of the molecular weight on the y-axis.

Below, there are two masses, namely essentially 26 kD and 21 kD, at more or less 20%, which each correspond to a cleaved form of the PSA. A certain proportion exists, between the cleaved and noncleaved forms of the free PSA, which may be used to differentiate cancer and BPH.

Figure 3:
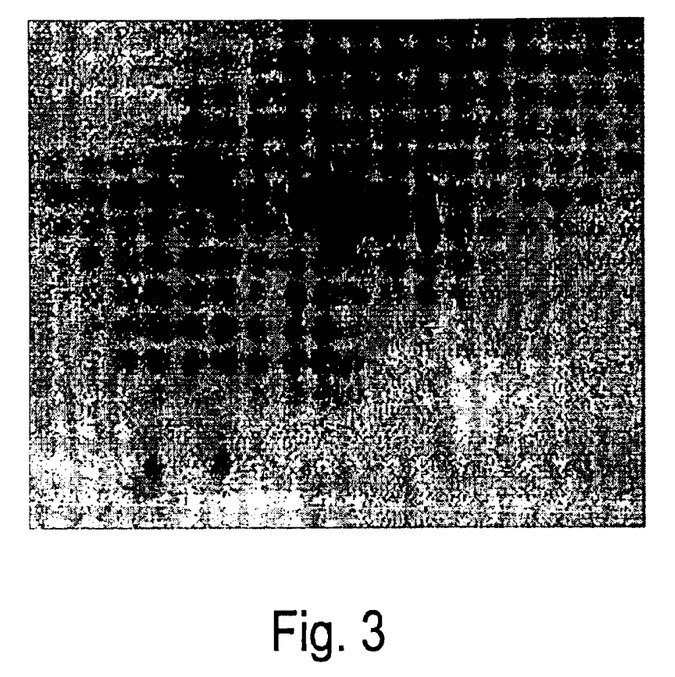
FIG. 3 represents a two-dimensional electro-phoresis of a serum from a patient suffering from a BPH, the serum containing 3.9 ng/ml of PSA.
Figure 4:
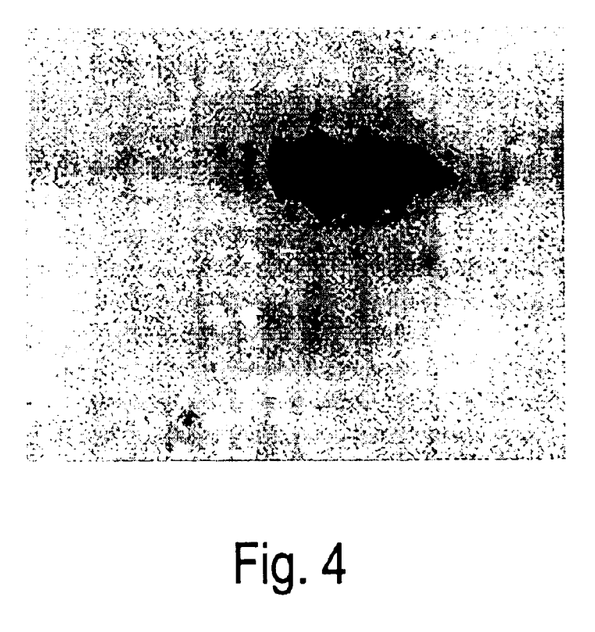
FIG. 4 represents a two-dimensional electro-phoresis of a serum from a patient suffering from an adenocarcinoma, the serum containing 4 000 ng/ml of PSA.

Thus, in the case of FIG. 3, the patient is suffering from a BPH and his serum of course contains 2.1 ng/ml of total PSA, that is exactly 3.9 ml. When this total PSA concentration is plotted on FIG. 1, it is observed that there is, at this level, both BPH cases and cancer cases. It is found that when the total free PSA, that is to say cleaved or noncleaved, is measured, that when the cleaved free PSA is also measured, a cleaved free PSA to total free PSA ratio can be calculated which makes it possible to make the diagnosis that the patient is suffering either from a cancer when this ratio is less than or greater than a reference value, or from a benign pathology of the prostate when said ratio is greater or less than this value.

Such values have already been described above and such a diagnostic method may also be applied:

to a ratio of the noncleaved free PSA concentration to the total free PSA concentration, or to a ratio of the cleaved free PSA concentration to the noncleaved free PSA concentration, or to a ratio of the cleaved free PSA concentration to the total PSA concentration, or finally to a ratio of the cleaved free PSA concentration to the complexed PSA concentration.

Figure 6:
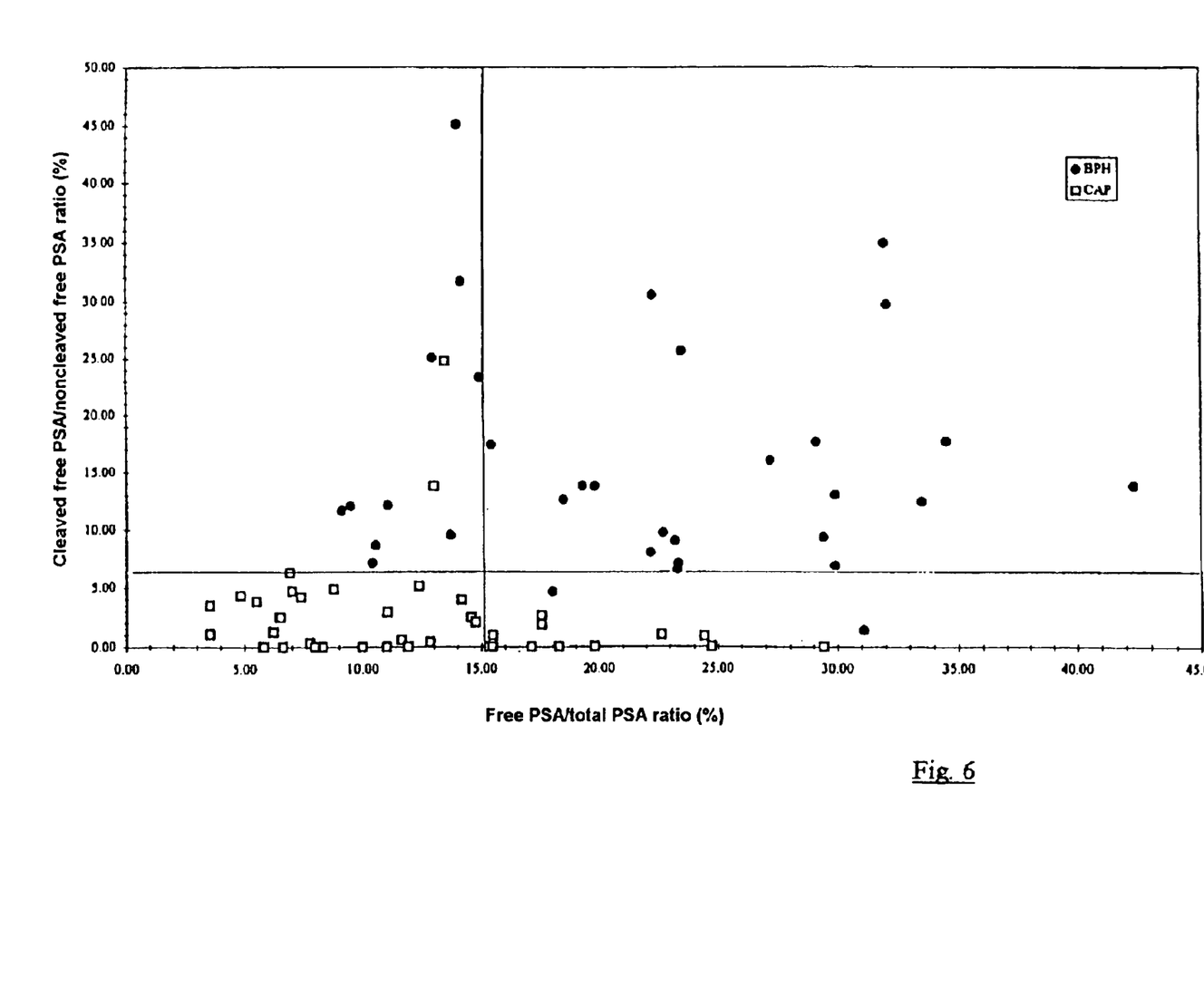
FIG. 6 represents a comparative table of the position of sera from different patients as a function, on the one hand, of their free PSA concentration to total PSA concentration ratio (x-axis), and, on the other hand, of their cleaved free PSA concentration to noncleaved free PSA ratio (y-axis). The open squares represent the cancer cases and the filled circles the BPH cases.

It is also possible to use a ratio of these ratios; that is for example the case in FIG. 6, with the ratio of the ratio of the free PSA concentration to the total PSA concentration to the ratio of the cleaved free PSA concentration to the noncleaved free PSA concentration. This will be developed later.

In general, one of these methods is to be carried out when the total PSA concentration, in the blood or in the serum, is greater than or equal to 2 ng/ml.

The method therefore consists in subjecting the proteins derived from the blood, serum, urine or seminal fluid of the patient to migration, in detecting the presence and in quantifying the free PSA in cleaved form or in noncleaved form and in determining if the patient is healthy or suffering from an adenocarcinoma of the prostate or from another benign pathology of the prostate according to the results obtained above.

The migration is generally carried out by two-dimensional electrophoresis and the detection by chemiluminescence with visualization by Western blotting. However, it is quite possible to envisage a technique using antibodies, which are either specific for the free PSA in cleaved form or specific for the free PSA in noncleaved form or possibly for the bound PSA, and which does not require migration prior to the detection of said forms.

All the results obtained are summarized in the table below:

| Serum | Pathology | TPSA | fPSA | cPSA | fPSA/TPSA | cPSA/ncPSA |
|---|---|---|---|---|---|---|
| Patient 1 | BPH | 3.90 | 0.87 | 0.20 | 22.31 | 30.55 |
| Patient 2 | BPH | 7.50 | 0.83 | 0.09 | 11.07 | 12.11 |
| Patient 3 | PCa | 11.00 | 1.21 | 0.00 | 11.00 | 0.00 |
| Patient 4 | PCa | 713.00 | 104.00 | 2.50 | 14.59 | 2.46 |
| Patient 5 | PCa | 3120.00 | 151.00 | 6.22 | 4.84 | 4.30 |
| Patient 6 | PCa | 4000.00 | 567.00 | 21.55 | 14.18 | 3.95 |
| Patient 7 | BPH | 9.13 | 2.84 | 0.04 | 31.11 | 1.37 |
| Patient 8 | BPH | 6.22 | 1.15 | 0.13 | 18.49 | 12.60 |
| Patient 9 | PCa | 7.07 | 1.24 | 0.03 | 17.54 | 2.61 |
| Patient 10 | BPH | 4.18 | 2.28 | 0.59 | 31.95 | 35.00 |
| Patient 11 | PCa | 10.5 | 0.84 | 0.00 | 8.00 | 0.00 |
| Patient 12 | BPH | 5.70 | 1.10 | 0.13 | 19.30 | 13.80 |
| Patient 13 | BPH | 9.68 | 2.82 | 0.42 | 29.13 | 17.66 |

-continued

| Serum | Path-ology | TPSA | fPSA | cPSA | fPSA/TPSA | cPSA/ncPSA |
|---|---|---|---|---|---|---|
| Patient 14 | PCa | 8.09 | 1.00 | 0.12 | 13.02 | 13.74 |
| Patient 15 | PCa | 10.55 | 2.09 | 0.00 | 19.81 | 0.00 |
| Patient 16 | PCa | 5.42 | 0.84 | 0.01 | 15.50 | 0.95 |
| Patient 17 | PCa | 10.00 | 0.69 | 0.04 | 6.90 | 6.30 |
| Patient 18 | PCa | 5.42 | 0.30 | 0.01 | 5.54 | 3.79 |
| Patient 19 | BPH | 5.55 | 1.00 | 0.04 | 18.02 | 4.64 |
| Patient 20 | BPH | 7.58 | 0.72 | 0.08 | 9.50 | 12.01 |
| Patient 21 | BPH | 4.16 | 0.97 | 0.06 | 23.32 | 6.56 |
| Patient 22 | BPH | 4.23 | 0.44 | 0.03 | 10.40 | 7.13 |
| Patient 23 | BPH | 8.27 | 3.50 | 0.42 | 42.32 | 13.80 |
| Patient 24 | PCa | 6.81 | 0.92 | 0.18 | 13.51 | 24.80 |
| Patient 25 | PCa | 29.83 | 1.73 | 0.00 | 5.80 | 0.00 |
| Patient 26 | PCa | 29.98 | 7.15 | 0.06 | 24.43 | 0.86 |
| Patient 27 | PCa | 4.98 | 0.29 | 0.00 | 5.82 | 0.00 |
| Patient 28 | BPH | 6.81 | 1.02 | 0.19 | 14.98 | 23.34 |
| Patient 29 | PCa | 5.66 | 0.70 | 0.03 | 12.37 | 5.13 |
| Patient 30 | PCa | 6.77 | 0.61 | 0.00 | 10.00 | 0.00 |
| Patient 31 | PCa | 7.9 | 1.79 | 0.02 | 22.66 | 0.97 |
| Patient 32 | PCa | 4.09 | 0.70 | 0.00 | 17.11 | 0.00 |
| Patient 33 | PCa | 26.51 | 3.16 | 0.00 | 11.92 | 0.00 |
| Patient 34 | PCa | 5.4 | 0.38 | 0.02 | 7.00 | 4.70 |
| Patient 35 | BPH | 1.27 | 0.19 | 0.05 | 14.18 | 31.72 |
| Patient 36 | BPH | 7.7 | 1.19 | 0.18 | 15.45 | 17.36 |
| Patient 37 | BPH | 5.24 | 0.72 | 0.06 | 13.74 | 9.51 |
| Patient 38 | BPH | 6.89 | 1.62 | 0.33 | 23.51 | 25.69 |
| Patient 39 | PCa | 9.58 | 1.23 | 0.00 | 12.84 | 0.36 |
| Patient 40 | BPH | 5.12 | 0.54 | 0.04 | 10.55 | 8.62 |
| Patient 41 | PCa | 7.07 | 1.24 | 0.02 | 17.54 | 1.84 |
| Patient 42 | BPH | 6.32 | 1.72 | 0.24 | 27.22 | 16.06 |
| Patient 43 | BPH | 7.67 | 2.57 | 0.28 | 33.51 | 12.42 |
| Patient 44 | PCa | 12.47 | 0.81 | 0.02 | 6.50 | 2.48 |
| Patient 45 | PCa | 10.57 | 0.70 | 0.00 | 6.62 | 0.00 |
| Patient 46 | PCa | 17.49 | 1.09 | 0.01 | 6.23 | 1.26 |
| Patient 47 | PCa | 10.84 | 2.56 | 0.00 | 18.29 | 0.00 |
| Patient 48 | PCa | 7.39 | 1.18 | 0.02 | 14.78 | 2.02 |
| Patient 49 | PCa | 40.39 | 10.00 | 0.00 | 24.76 | 0.00 |
| Patient 50 | PCa | 11.43 | 0.89 | 0.00 | 7.79 | 0.32 |
| Patient 51 | PCa | 46.46 | 3.43 | 0.14 | 7.38 | 4.17 |
| Patient 52 | BPH | 5.03 | 0.46 | 0.05 | 9.15 | 11.65 |
| Patient 53 | BPH | 4.01 | 0.52 | 0.10 | 12.97 | 25.11 |
| Patient 54 | PCa | 5.62 | 0.20 | 0.00 | 3.56 | 1.11 |
| Patient 55 | PCa | 9.5 | 0.34 | 0.00 | 3.58 | 1.07 |
| Patient 56 | BPH | 6.22 | 1.86 | 0.12 | 29.90 | 6.89 |
| Patient 57 | BPH | 2.42 | 0.74 | 0.07 | 22.73 | 9.71 |
| Patient 58 | BPH | 5.8 | 1.86 | 0.43 | 32.07 | 29.79 |
| Patient 59 | BPH | 4.52 | 1.05 | 0.09 | 23.23 | 9.01 |
| Patient 60 | BPH | 6.22 | 1.86 | 0.21 | 29.90 | 13.02 |
| Patient 61 | PCa | 4.63 | 0.71 | 0.00 | 15.33 | 0.00 |
| Patient 62 | PCa | 13.01 | 2.58 | 0.00 | 8.32 | 0.00 |
| Patient 63 | PCa | 33.96 | 10.00 | 0.00 | 29.45 | 0.00 |
| Patient 64 | PCa | 58.82 | 6.84 | 0.04 | 11.63 | 0.56 |
| Patient 65 | PCa | 20.29 | 3.15 | 0.09 | 11.04 | 2.92 |
| Patient 66 | BPH | 5.01 | 1.17 | 0.08 | 23.35 | 7.10 |
| Patient 67 | BPH | 16 | 2.24 | 0.70 | 14.00 | 45.13 |
| Patient 68 | BPH | 4.55 | 1.01 | 0.07 | 22.20 | 8.01 |
| Patient 69 | BPH | 5.20 | 1.53 | 0.13 | 29.42 | 9.34 |
| Patient 70 | BPH | 7.21 | 1.43 | 0.17 | 19.83 | 13.77 |
| Patient 71 | PCa | 5.56 | 0.86 | 0.00 | 15.47 | 0.00 |
| Patient 72 | PCa | 5.62 | 0.20 | 0.01 | 3.56 | 3.45 |
| Patient 73 | PCa | 98.82 | 7.68 | 0.03 | 7.77 | 0.33 |
| Patient 74 | PCa | 18.41 | 1.64 | 0.08 | 8.78 | 4.87 |
| Patient 75 | BPH | 4.29 | 1.48 | 0.22 | 34.50 | 17.71 |

This is a comparative study between the sera of seventy-five different patients.

In order to clearly understand the above table, it should be noted that the concentrations of total PSA (TPSA), free PSA (fPSA) and cleaved PSA (cPSA) are expressed in ng/ml. The ratios, for their part, are expressed as a percentage.

This table makes it possible to visualize rapidly the ratios which exist between:

the, concentration of total PSA, designated hereinafter by the reference TPSA, the concentration of PSA bound to protease inhibitors, such as ACT, designated hereinafter by the reference bPSA, the concentration of free PSA, designated hereinafter by the reference fPSA, the concentration of noncleaved free PSA, designated hereinafter by the reference ncPSA, and the concentration of cleaved free PSA, designated hereinafter by the reference cPSA.

It should be noted that the concentration of noncleaved PSA (ncPSA) is used in the right-hand column. Even if it is not given, it can be easily deduced from the following equation:

$$ncPSA = fPSA - cPSA$$

When the fPSA/TPSA ratio is taken into account, it is observed that this ratio is not at all characteristic. Thus, out of the first six patients, only patients 1 and 5 have a characteristic ratio, that is to say that it could make it possible to distinguish a cancer case from a BPH case.

In the other cases, the ratios are between 11.00 and 14.59. Discrimination between cancer and BPH is not therefore possible. This is also true with the other sera from patients. It is for example very difficult to differentiate between patients 8 and 9, 12 and 15, and the like.

Particularly striking examples are the cases of patients 22, 40 and 52 who are suffering from a BPH with an fPSA/TPSA ratio always less than 11, whereas over the same period, patients 26, 31, 49 and 63 are suffering from a cancer by having a ratio which is always greater than 22. Between these values of 11 and 22, there is therefore a blurred zone in respect of the diagnosis. However, numerous sera are in this zone (or even beyond as is the case for the seven patients which have just been described). The number of sera in this zone is thirty-one, that is a total of thirty-eight sera not diagnosed with an efficient probability. This represents an error of substantially 50.67%. The use of the fPSA/TPSA ratio is in this case unsuitable for distinguishing between BPH and cancer.

This clearly shows the limits of this technique.

If on the other hand the ratios which exist between cPSA/bPSA, cPSA/TPSA, ncPSA/fPSA, cPSA/fPSA and cPSA/ncPSA are used, and still with reference to the first six sera from patients, it is observed that there is a large difference between the ratios for patients 1 and 2 suffering from a BPH and patients 3 to 6 suffering from a cancer.

These ratios, which use the cleaved and/or noncleaved forms of the PSA, are therefore considerably more representative of the real condition of a patient.

Thus, in the context of the examples taken from the table, with the CPSA/TPSA ratio, in the case of a BPH, the ratio is always greater than or equal to 1.2% and in the case of a cancer, the ratio is always less than 0.54%.

With the cPSA/bPSA ratio, in the case of a BPH, the ratio is always greater than 1.34% and in the case of a cancer, the ratio is always less than 0.63%.

With the ncPSA/fPSA ratio, in the case of a BPH, the ratio is always less than 89.2% and in the case of a cancer, the ratio is always greater than 95.88%.

With the cPSA/fPSA ratio, in the case of a BPH, the ratio is always greater than 10.8% and in the case of a cancer, the ratio is always less than 4.12%.

Finally, with the cPSA/ncPSA ratio, in the case of a BPH, the ratio is always greater than 12.11% and in the case of a cancer, the ratio is always less than 4.3%.

The ratios, which are not representative, consist of the ratios ncPSA/TPSA, ncPSA/bPSA and fPSA/TPSA since the ratios for the three patients 3, 4 and 6, suffering from cancer, is in the range delimited by the ratios for patients 1 and 2, suffering from a BPH.

Because of this, it may be particularly advantageous to use a combination of different ratios, cPSA/TPSA, cPSA/bPSA, ncPSA/fPSA, cPSA/fPSA and cPSA/ncPSA, or even all these ratios, to differentiate a benign pathology of the prostate relative to a cancer of the prostate.

When patients 22, 40 and 52 are considered, it is observed that their cPSA/ncPSA ratio is 7.13 –8.62–11.65, respectively. As regards patients 26, 31, 49 and 63, their cPSA/ncPSA ratio is then 0.86 –0.97–0.00–0.00, respectively.

The ratio is therefore perfectly suited to the diagnosis which practitioners wish carried out.

Figure 5:
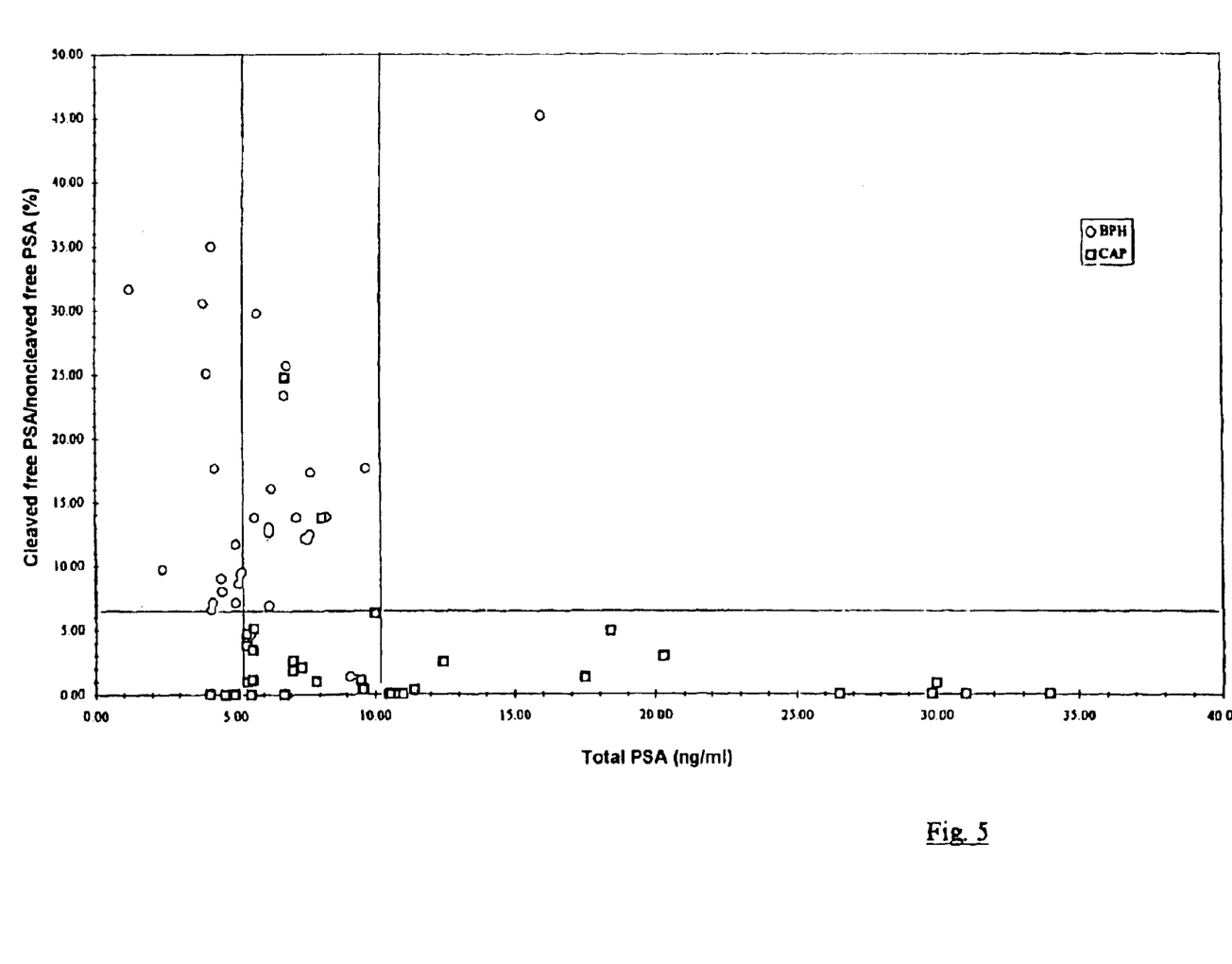
FIG. 5 represents a comparative table of the position of sera from different patients as a function, on the one hand, of their total PSA concentration, which is between 1 and 34 ng/ml (x-axis) and, on the other hand, of their cleaved free PSA concentration to noncleaved free PSA concentration ratio (y-axis). The open squares represent the cancer cases and the filled circles the BPH cases.

If reference is now made to FIG. 5, it will be noted that above a horizontal straight line corresponding to 6.5% of the cPSA/ncPSA ratio, practically all the BPH cases are represented, with the exception of two cases. They are patients 7 and 19 for whom the ratios are 1.37 and 4.64, that is two cases out of thirty-three, that is to say that the error is substantially 6%, which is considerably less than the conventional fPSA/TPSA ratio seen above.

It will also be observed that below this reference horizontal straight line situated at 6.5% of the cPSA/ncPSA ratio, practically all the cancer cases are represented, with the exception of two cases. They are patients 14 and 24 for whom the ratios are 13.74 and 24.80, that is two cases out of forty-two, that is to say that the error is essentially 4.77%.

FIG. 6 is even more vivid. Two straight lines are observed, one vertical and the other horizontal, which intersect. The vertical straight line corresponds to the value of 15.1% of the fPSA/TPSA ratio and the horizontal straight line corresponds to the value of 6.2% of the cPSA/ncPSA ratio. Four cases may be deduced, they are:

this cPSA/ncPSA ratio has a value of less than or equal to 6.2% and this fPSA/TPSA ratio has a value of less than or equal to 15.1%, such that the patient is suffering from an adenocarcinoma of the prostate, this cPSA/ncPSA ratio has a value greater than 6.2% and this fPSA/TPSA ratio has a value greater than 15.1%, such that the patient is suffering from a benign pathology of the prostate, such as a benign prostate hyperplasia, this cPSA/ncPSA ratio has a value of less than or equal to 6.2% and this fPSA/TPSA ratio has a value greater than 15.1%, such that the patient has a high probability of suffering from an adenocarcinoma of the prostate and a low probability of suffering from a benign pathology of the prostate, such as a benign prostate hyperplasia, this cPSA/ncPSA ratio has a value greater than 6.2%, this fPSA/TPSA ratio has a value of less than or equal to 15.1%, such that the patient has a high probability of suffering from a benign pathology of the prostate, such as a benign prostate hyperplasia, and a low probability of suffering from an adenocarcinoma of the prostate.

Even if the reference values are given at 6.2 and 15.1%, it is possible for these figures to vary with another panel of sera or a different number of sera. Therefore, preferably, the first reference value is between 1 and 18%, preferably between 5 and 8%, and the second reference value is between 10 and 20%, preferably between 13 and 17%.

As regards the probabilities mentioned above, in the third case described above, the high probability of suffering from an adenocarcinoma of the prostate is between 84 and 87% and the low probability of suffering from a benign pathology of the prostate is between 13 and 16%. Thus, there are two cases of BPH out of fourteen in total. However, for these third and fourth cases, these values may be broadened because with other samples a broader range may be found, for example 80 to 95% for the high probability, and 5 to 20% for the low probability.

In the fourth case, the high probability of suffering from a benign pathology of the prostate is between 82 and 85%, and the low probability of suffering from an adenocarcinoma of the prostate is between 15 and 18%. This corresponds to two cases of cancers per twelve cases in total.

However, for these third and fourth cases, these values may be broadened because with other samples, a broader range may be found, for example 80 to 95% for the high probability, and 5 to 20% for the low probability.

We have available three independent variables:

A=bPSA, that is to say the PSA complexed or bound to inhibitors (ACT and the like)

B=ncPSA, that is to say the noncleaved free PSA

C=cPSA, that is to say the cleaved free PSA with concentrations such that A>>B>>C Consequently, the different ratios may be written in the following manner and may lead to the following approximations:

$$1.\ \frac{fPSA}{TPSA} = \frac{B+C}{A+B+C} \approx \frac{B}{A}$$

$$2.\ \frac{ncPSA}{TPSA} = \frac{B}{A+B+C} \approx \frac{B}{A}$$

$$3.\ \frac{cPSA}{TPSA} = \frac{C}{A+B+C} \approx \frac{C}{A}$$

$$4.\ \frac{ncPSA}{bPSA} = \frac{B}{A}$$

$$5.\ \frac{cPSA}{bPSA} = \frac{C}{A}$$

$$6.\ \frac{ncPSA}{fPSA} = \frac{B}{B+C} = 1 - \frac{C}{B+C} = 1 - \frac{1}{1+\frac{B}{C}} \approx 1 - \frac{C}{B}$$

$$7.\ \frac{cPSA}{fPSA} = \frac{C}{B+C} = \frac{1}{1+\frac{B}{C}} \approx \frac{C}{B}$$

$$8.\ \frac{cPSA}{ncPSA} = \frac{C}{B}$$

It therefore appears that the ratios 1, 2 and 4 lead to the -same type of response. The ratio 1 has already been described in the prior state of the art, which was discussed above, and leads to many false diagnoses; consequently, the ratios 2 and 4 are not of interest.

The ratios 6, 7 and 8 are linked by a precise mathematical relationship which amounts to saying that they make it possible to arrive at an identical response.

The ratios 3 and 5 lead to an equivalent response different from the preceding ratios.

The ratios 3 and 5 to 8 are therefore representative.

Several strategies exist for assaying cleaved or non-cleaved free PSA.

Cleaved PSA has the following characteristics.

Firstly, the internal fragmentation sites do not affect the three-dimensional cohesion of the molecule because of the existence of five disulfide bridges which link the various fragments. Secondly, after reduction, these disulfide bridges are broken and the various PSA fragments dissociate. Thirdly, the fragmentations modify the conformation of the PSA and cause it to lose its enzymatic activity and its capacity to bind to protease inhibitors.

I—Assay of the Cleaved Forms After Reduction of the Sample:

After fragmentation or cleavage and reduction, internal PSA zones are unmasked and inaccessible epitopes on the full-length PSA are revealed. Cleaved and reduced PSA or peptides situated before and after the cleavage sites comprise such epitopes. Immunizations with these peptides or cleaved and reduced PSA make it possible to obtain antibodies directed against the desired epitopes. After reduction of the sample to be analyzed, a test using such antibodies specifically assays the cleaved PSA.

Thus, a cleaved and reduced PSA immunogen was obtained and characterized. Peptides situated before or after the cleavage sites were synthesized. Immunization with cleaved and reduced PSA was carried out on mice. Ten monoclonal antibody clones specific for the epitopes characteristic of the cleaved PSA were obtained II—Assay of the Cleaved Forms without Reduction of the Sample:

The cleaved PSA is inactive and may comprise a conformational modification responsible for the loss of activity. Immunization of mice with this PSA can make it possible to obtain antibodies directed against these conformational epitopes. A test using these antibodies assays the cleaved PSA directly and specifically.

Predominantly cleaved inactive PSA was obtained from a supplier. Immunization was carried out on mice.

III—Assay of Noncleaved PSA After Reduction of the Sample:

After reduction of the sample, the cleaved PSA fragments whereas the amino acid chain of the noncleaved PSA remain intact. C-terminal and N-terminal peptides make it possible to carry out a detection specifically of the antibodies directed against the C-terminal part or the N-terminal part or to obtain them after immunization. After reduction of the sample, a sandwich with an antibody directed against the C-terminal part and an antibody directed against the N-terminal part would make it possible to recognize the full-length PSA.

C-terminal and N-terminal peptides of the PSA were obtained. These peptides were used in order to demonstrate immunizations on mice carried out with seminal PSA or to immunize mice directly. Antibodies were detected in order to define pairs recognizing the noncleaved reduced PSA and not the cleaved reduced PSA.

We have available some pairs of antibodies having the expected characteristics as is clearly represented by the Optical Density Values in the table below:

| Monoclonal antibody | Noncleaved reduced PSA at 100 ng/ml | Cleaved reduced PSA at 100 ng/ml |
| --- | --- | --- |
| 4H10B4 | >2 | 0.133 |
| 21D7C1 | >2 | 0.103 |
| 1C7H10 | >2 | 0.121 |
| 12E6H9 | 1.803 | 0.082 |

IV—Assay of the Noncleaved PSA Under Nonreducing Condition:

The noncleaved PSA may comprise certain conformational epitopes different from the cleaved PSA (reference to section II). Peptides overlapping the fragmentation sites may exhibit such epitopes. Immunization on mice with these peptides or with noncleaved PSA makes it possible to obtain antibodies directed against these epitopes. A test, using these antibodies, assays the noncleaved PSA directly and specifically.

The peptides were synthesized. Immunization with predominantly noncleaved PSA was carried out on mice.

V—Assay of the Enzymatically Active PSA:

The noncleaved PSA in the serum may be enzymatically active. Thus, it was demonstrated that the cleaved PSA was enzymatically inactive but not the opposite. An inhibitory peptide having a high affinity for active PSA may be designed by phage display and/or modification of natural sequences. The peptide thus designed may be used to selectively capture the enzymatically active PSA and thus allow its assay.

The protocol which follows allows the specific assay of the noncleaved PSA. It consists in carrying out the following operations:

Coating of ELISA microplate with 100 µl of antibody at 20 µg/ml in 0.2 M Tris Maleate buffer, pH=6.2.

Incubation overnight at room temperature.

Washing with 3 times 300 µl of 0.2 M Tris Maleate buffer, 0.5% Tween 20, pH=6.2

Passivation for 1 hour with 200 µl of 0.2 M Tris Maleate buffer, 3% fetal calf serum, pH=6.2.

Washing with 3 times 300 µl of 0.2 M Tris Maleate buffer, 0.5% Tween 20, pH=6.2

Dilution of the PSA to 100 µg/ml in 0.2 M Tris Maleate buffer, 3% fetal calf serum, pH=6.2.

Incubation of 100 µl of PSA for 1 hour at 37° C.

Washing with 3 times 300 µl of 0.2 M Tris Maleate buffer, 0.5% Tween 20, pH=6.2

Incubation for 1 hour at 37° C. of 100 µl of anti-biotinylated PSA antibody 3A1B5, diluted 1/1000 in 0.2 M Tris Maleate buffer, 3% fetal calf serum, pH=6.2.

Washing with 3 times 300 µl of 0.2 M Tris Maleate buffer, 0.5% Tween 20, pH=6.2

Incubation for 1 hour at 37° C. of 100 µl of streptavidin-alkaline phosphatase, diluted 1/500 in 0.2 M Tris buffer containing 0.1 M NaCl, 1 mM $MgCl_2$, 0.1 mm $ZnCl_2$, 3% fetal calf serum, pH=6.5.

Washing with 3 times 300 µl of 0.2 M Tris Maleate buffer, 0.5% Tween 20, pH=6.2

Visualization for 15 minutes at 37° C. with 100 µl of pNPP substrate

Blocking of the reaction with 100 µl of 1 N sodium hydroxide.

Reading on a spectrophotometer at 405 nm with subtraction of the background noise at 630 nm.

What is claimed is:

1. Method of analyzing PSA (prostate specific antigen) protein ratios present in a blood, serum, urine or seminal fluid sample of a male patient, for the purpose of diagnosing an adenocarcinoma of the prostate or a benign prostate hyperplasia (BPH), said method comprising:

measuring a level of total free PSA in the sample, wherein the total free PSA consists of cleaved and non-cleaved free PSA, measuring the level of cleaved free PSA in the sample, calculating a patient ratio of the cleaved free PSA level relative to the total free PSA level, comparing the patient ratio to a reference value, wherein the reference value is a ratio of cleaved free PSA levels relative to total free PSA levels found in patients suffering from adenocarcinoma of the prostate, and wherein the reference value is between 2% and 12%, interpreting a patient ratio greater than the reference value as an indication that the patient has a benign prostate hyperplasia, and interpreting a patient ratio less than or equal to the reference value as an indication that the patient has an adenocarcinoma of the prostate.

2. Method according to claim 1, wherein the reference value is between 5% and 8%.

3. Method according to claim 1, wherein the reference value is between 5% and 6.2%.

4. Method according to claim 1, wherein the reference value is approximately 6%.

5. Method according to claim 1, wherein said method is used in combination with at least one additional method of analyzing PSA protein ratios present in a male patient sample.

6. Method according to claim 1, wherein said method is used in combination with at least one additional method of diagnosing a benign prostate hyperplasia or adenocarcinoma of the prostate of a male patient.

7. Method for analyzing PSA (prostate specific antigen) protein ratios in a blood, serum, urine or seminal fluid sample of a male patient, for the purpose of diagnosing an adenocarcinoma of the prostate, said method comprising:

measuring a level of total free PSA in the sample, wherein the total free PSA consists of cleaved and non-cleaved PSA, measuring a level of cleaved free PSA in the sample, calculating a patient ratio of the cleaved free PSA level relative to the total free PSA level, comparing the patient ratio to a reference value, wherein the reference value is a ratio of cleaved free PSA levels relative to total free PSA levels found in patients suffering from adenocarcinoma of the prostate, and wherein the reference value is between 2% and 12%, and interpreting a patient ratio less than or equal to the reference value as an indication that the patient has an adenocarcinoma of the prostate.

8. Method according to claim 7, wherein the reference value is between 5% and 8%.

9. Method according to claim 7, wherein said method is used in combination with at least one additional method of analyzing PSA protein ratios present in a male patient sample.

10. Method according to claim 7, wherein said method is used in combination with at least one additional method of diagnosing an adenocarcinoma of the prostate of a male patient.

* * * * *